(12) United States Patent
Pinchuk

(10) Patent No.: US 7,794,498 B2
(45) Date of Patent: Sep. 14, 2010

(54) OCULAR LENS

(75) Inventor: Leonard Pinchuk, Miami, FL (US)

(73) Assignee: Innolene LLC, Miami, FL (US)

( * ) Notice: Subject to any disclaimer, the term of this patent is extended or adjusted under 35 U.S.C. 154(b) by 746 days.

(21) Appl. No.: 11/004,538

(22) Filed: Dec. 3, 2004

(65) Prior Publication Data
US 2005/0125059 A1 Jun. 9, 2005

Related U.S. Application Data

(60) Provisional application No. 60/526,965, filed on Dec. 5, 2003, provisional application No. 60/526,966, filed on Dec. 5, 2003.

(51) Int. Cl.
*A61F 2/16* (2006.01)
(52) U.S. Cl. ............ 623/6.56; 351/159; 523/106; 424/427
(58) Field of Classification Search .......... 623/6.4, 623/6.56, 6.58; 351/159; 424/427; 523/106, 523/113
See application file for complete search history.

(56) References Cited

U.S. PATENT DOCUMENTS

| | | | | |
|---|---|---|---|---|
| 2,674,743 A * | 4/1954 | Gaiser et al. | ............ | 623/6.64 |
| 4,186,184 A * | 1/1980 | Zaffaroni | ............ | 424/427 |
| 4,254,509 A * | 3/1981 | Tennant | ............ | 623/6.37 |
| 4,276,394 A * | 6/1981 | Kennedy et al. | ............ | 525/245 |
| 4,298,996 A | 11/1981 | Barnet | ............ | 623/6.43 |
| 4,315,337 A * | 2/1982 | Choyce | ............ | 623/6.43 |
| 4,316,973 A * | 2/1982 | Kennedy | ............ | 525/333.7 |
| 4,342,849 A * | 8/1982 | Kennedy | ............ | 525/333.7 |
| 4,452,776 A * | 6/1984 | Refojo | ............ | 514/772.4 |
| 4,578,078 A * | 3/1986 | Arkell et al. | ............ | 623/6.51 |
| 4,601,720 A * | 7/1986 | Sinskey | ............ | 623/6.54 |
| 4,661,573 A * | 4/1987 | Ratkowski et al. | ............ | 526/245 |

(Continued)

FOREIGN PATENT DOCUMENTS

WO WO02/47731 6/2002

(Continued)

OTHER PUBLICATIONS

The Sandwich Theory, Reijo Linnola, Dept. of Opthalamology, Dept. of Medical Biochemistry, Collagen Research Unit, University of Oulu, 2001.

(Continued)

*Primary Examiner*—Paul Prebilic
(74) *Attorney, Agent, or Firm*—Gordon & Jacobson, PC

(57) ABSTRACT

An ocular lens has a refractive optics structure formed from a polyisobutylene-based material and a glassy segment that is non-reactive to ocular fluid and that maintains in vivo transparency for a substantial time period. The material has a central elastomeric polyolefinic block and thermoplastic end blocks (such as a triblock polymer backbone comprising polystyrene-polyisobutylene-polystyrene). The material is preferably flexible such that the refractive optics structure can be folded upon itself and introduced through a small scleral incision. The lens device includes an optic portion and preferably either an annular haptic element or one or more haptic elements adapted to rest within a capsular bag formed by a surgical procedure. A portion of the lens device may be loaded with at least one therapeutic agent that interferes with proliferation of the epithelial cells of the eye to protect against PCO.

27 Claims, 7 Drawing Sheets

U.S. PATENT DOCUMENTS

| | | | |
|---|---|---|---|
| 4,704,123 A * | 11/1987 | Smith | 623/6.43 |
| 4,752,627 A | 6/1988 | Froix | |
| 4,842,601 A | 6/1989 | Smith | 623/6.34 |
| 4,886,866 A * | 12/1989 | Braatz et al. | 528/59 |
| 4,897,255 A | 1/1990 | Fritzberg et al. | 530/391.5 |
| 4,904,421 A * | 2/1990 | Ando et al. | 264/2.6 |
| 4,910,321 A * | 3/1990 | Kennedy et al. | 549/213 |
| 4,929,683 A * | 5/1990 | Kennedy et al. | 525/268 |
| 4,936,825 A * | 6/1990 | Ungerleider | 604/8 |
| 4,946,899 A * | 8/1990 | Kennedy et al. | 525/244 |
| 4,963,148 A | 10/1990 | Sulc et al. | 623/6.23 |
| 4,994,082 A | 2/1991 | Richards et al. | 623/6.32 |
| 5,047,051 A | 9/1991 | Cumming | 623/6.45 |
| 5,066,730 A * | 11/1991 | Kennedy et al. | 525/319 |
| 5,122,572 A * | 6/1992 | Kennedy et al. | 525/314 |
| 5,275,623 A | 1/1994 | Sarfarazi | 623/6 |
| RE34,640 E * | 6/1994 | Kennedy et al. | 525/244 |
| 5,681,869 A * | 10/1997 | Villain et al. | 522/84 |
| 5,730,156 A * | 3/1998 | Mackool | 128/898 |
| 5,733,925 A | 3/1998 | Kunz | 514/449 |
| 5,741,331 A * | 4/1998 | Pinchuk | 424/423 |
| 5,789,463 A * | 8/1998 | Odagiri et al. | 523/106 |
| 6,027,531 A | 2/2000 | Tassignon | 623/6 |
| 6,050,970 A * | 4/2000 | Baerveldt | 604/28 |
| 6,102,939 A * | 8/2000 | Pinchuk | 623/23.58 |
| 6,158,862 A * | 12/2000 | Patel et al. | 351/164 |
| 6,187,042 B1 | 2/2001 | Sheets, Jr. et al. | 623/6.62 |
| 6,197,059 B1 | 3/2001 | Cumming | 623/6.39 |
| 6,197,240 B1 * | 3/2001 | Pinchuk | 264/309 |
| 6,271,281 B1 * | 8/2001 | Liao et al. | 523/106 |
| 6,331,313 B1 | 12/2001 | Wong et al. | 424/427 |
| 6,391,056 B2 * | 5/2002 | Cumming | 623/6.43 |
| 6,468,283 B1 * | 10/2002 | Richter et al. | 606/108 |
| 6,545,097 B2 * | 4/2003 | Pinchuk et al. | 525/240 |
| 6,569,195 B2 | 5/2003 | Yang et al. | 623/1.46 |
| 6,626,858 B2 * | 9/2003 | Lynch et al. | 604/8 |
| 6,685,741 B2 | 2/2004 | Landreville et al. | 623/6.37 |
| 6,692,525 B2 | 2/2004 | Brady et al. | 623/6.18 |
| 6,695,881 B2 | 2/2004 | Peng et al. | 623/6.34 |
| 6,713,080 B1 | 3/2004 | Aiache et al. | 424/427 |
| 6,726,323 B2 | 4/2004 | Miyamura et al. | 351/160.4 |
| 6,732,994 B2 | 5/2004 | Sarbadhikari | 249/134 |
| 6,736,791 B1 * | 5/2004 | Tu et al. | 604/8 |
| 6,855,770 B2 * | 2/2005 | Pinchuk et al. | 525/240 |
| 2002/0107330 A1 * | 8/2002 | Pinchuk et al. | 525/242 |
| 2003/0194421 A1 * | 10/2003 | Signore | 424/426 |
| 2004/0056371 A1 * | 3/2004 | Liao et al. | 264/2.5 |
| 2004/0102758 A1 | 5/2004 | Davilla et al. | 604/500 |
| 2004/0158323 A1 | 8/2004 | Lisk, Jr. et al. | |
| 2004/0185268 A1 * | 9/2004 | Kumar et al. | 428/446 |
| 2005/0055075 A1 * | 3/2005 | Pinchuk et al. | 623/1.1 |
| 2005/0165488 A1 * | 7/2005 | Hunter et al. | 623/17.16 |
| 2005/0168689 A1 * | 8/2005 | Knox | 351/163 |

FOREIGN PATENT DOCUMENTS

| | | | |
|---|---|---|---|
| WO | WO 02/47731 A2 * | 6/2002 | |

OTHER PUBLICATIONS

"Presbyopia research shows polymer gel implants and zoom-opti IOLs hold promise" Internet Article EyeWorld Apr. 2004; www.eyeworld.org.

"Complications of Cataract Surgery"; Baush & Lomb; Sep. 7, 2001; Internet article; www.optometry.co.uk.

"Paclitaxel as a Locally Delivered Therapy to Prevent Restenosis"; Dr. A. Heldman; Mar. 29, 2004; Boston Scientific.

* cited by examiner

OCULAR LENS

CROSS-REFERENCE TO RELATED APPLICATIONS

The present application claims priority from U.S. Provisional Patent Application 60/526,965, filed Dec. 5, 2003 and U.S. Provisional Patent Application 60/526,966, filed Dec. 5, 2003, both herein incorporated by reference in their entirety.

BACKGROUND OF THE INVENTION

1. Field of the Invention

This invention relates broadly to ocular lens devices. More particularly, this invention relates to intraocular lens devices that are surgically implanted within the capsular bag of a human eye.

2. State of the Art

The human eye has an anterior chamber between the cornea and the iris, a posterior chamber behind the iris containing a crystalline lens, a vitreous chamber behind the lens containing vitreous humor, and a retina at the rear of the vitreous chamber. The crystalline lens of a normal human eye has a lens matrix in addition to a lens capsule attached about its periphery to the ciliary muscle of the eye by zonules. This lens capsule has elastic optically clear anterior and posterior membrane-like walls, which are commonly referred by ophthalmologists as anterior and posterior capsules, respectively. Between the iris and ciliary muscle is an annular space called the ciliary sulcus.

The human eye possesses natural accommodation capability. Natural accommodation involves relaxation and constriction of the ciliary muscle by the brain to provide the eye with near and distant vision. This ciliary muscle action is automatic and shapes the natural crystalline lens to the appropriate optical configuration for focusing the light rays entering the eye onto the retina.

The human eye is subject to a variety of disorders which degrade, or totally destroy, the ability of the eye to function properly. One of the more common of these disorders involves progressive clouding of the crystalline lens matrix resulting in the formation of what is referred to as a cataract.

It is common practice to cure a cataract by surgically removing the clouded crystalline lens and implanting an artificial intraocular lens in the eye to replace the natural lens. The prior art is replete with a vast assortment of intraocular lenses. Examples of such lenses are described in the following patents: U.S. Pat. Nos. 4,254,509, 4,298,996, 4,842,601, 4,963,148, 4,994,082, and 5,047,051. As is evident from the above patents, intraocular lenses differ widely in their physical appearance and arrangement.

Typically, cataracts are surgically removed by anterior capsulotomy, which involves forming an incision in the sclera beneath the cornea. Tooling is inserted through this incision and manipulated to open the anterior capsule of the natural lens while leaving intact a capsular bag. This capsular bag has an elastic posterior capsule, an anterior capsular remnant or rim about the anterior capsule opening and a capsular bag sulcus. The capsular bag sulcus is located between the anterior capsule remnant and the outer circumference of the posterior capsule. The capsular bag remains attached about its periphery to the surrounding ciliary muscle of the eye by the zonules of the eye. The lens matrix is extracted from the capsular bag through the scleral incision by phacoemulsification and aspiration (or in some other way). An intraocular lens is then implanted through the scleral incision such that it lies within the capsular bag.

A relatively recent and improved form of anterior capsulotomy known as capsulorhexis forms a generally circular-shaped opening through the anterior capsule by tearing the anterior capsule of the natural lens capsule along a generally circular tear line substantially coaxial with the lens axis and removing the generally circular portion of the anterior capsule surrounded by the tear line. If performed properly, capsulorhexis provides a generally circular opening through the anterior capsule of the natural lens capsule substantially coaxial with the axis of the eye and surrounded circumferentially by a continuous annular remnant or rim of the anterior capsule having a relatively smooth and continuous inner edge bounding the opening.

Another anterior capsulotomy procedure, referred to as an envelope capsulotomy, forms a generally arch-shaped opening through the anterior capsule by cutting a horizontal incision in the anterior capsule, then cutting two vertical incisions in the anterior capsule intersecting and rising from the horizontal incision, and finally tearing the anterior capsule along a tear line having an upper upwardly arching portion which starts at the upper extremity of the vertical incision and continues in a downward vertical portion parallel to the vertical incision which extends downwardly and then across the second vertical incision. This procedure produces a generally arch-shaped anterior capsule opening centered on the axis of the eye. The opening is bounded at its bottom by the horizontal incision, at one vertical side by the vertical incision, at its opposite vertical side by the second vertical incision of the anterior capsule, and at its upper side by the upper arching portion of the capsule tear.

Another capsulotomy procedure, typically referred to as can opener capsulotomy, forms a generally circular-shaped opening through the anterior capsule by piercing the anterior capsule at a number of positions along a circular line substantially coaxial with the axis of the eye and then removing the generally circular portion of the anterior capsule circumferentially surrounded by the line. This procedure produces a generally circular anterior capsule opening substantially coaxial with the axis of the eye and bounded circumferentially by an annular remnant or rim of the anterior capsule.

Intraocular lenses differ widely in their physical appearance and arrangement, yet generally have a central optical region (or optic) and haptics which extend outward from the optic and engage the interior of the eye in such a way as to support the optic in a position centered on the axis of the eye. Intraocular lenses also differ with respect to their accommodation capability, and their placement in the eye. Accommodation is the ability of an intraocular lens to accommodate, that is to focus the eye for near and distant vision. Most non-accommodating lenses have single focus optics, which focus the eye at a certain fixed distance only and require the wearing of eyeglasses to change the focus. Other non-accommodating lenses have bifocal optics which image both near and distant objects on the retina of the eye. The brain selects the appropriate image and suppresses the other image, so that a bifocal intraocular lens provides both near vision and distant vision sight without eyeglasses. Bifocal intraocular lenses, however, suffer from the disadvantage that 20% of the available light is lost in scatter, thereby providing lessened visual acuity. Newer intraocular lenses, such as the intraocular lens described in U.S. Pat. No. 6,685,741, achieve multifocal accommodation in response to compressive forces exerted on the haptics of the lens. Such compressive forces are derived from natural brain-induced contraction and relaxation of the ciliary muscle and increases and decreases in vitreous pressure. Such accommodating intraocular lenses are surgically implanted within the evacuated capsular bag of the patient's eye through the scleral incision and anterior capsule opening in the capsular bag. The haptics of the lens are situated within the outer perimeter of the capsular bag and are designed to support the optics along the optical axis of the eye in a manner that minimizes stretching of the capsular bag.

After surgical implantation of the intraocular lens in the capsular bag of the eye, active endodermal cells on the posterior side of the anterior capsule rim of the capsular bag causes fusion of the rim to the elastic posterior capsule wall by fibrosis. This fibrosis occurs about the haptics of the IOL in such a way that the haptics are effectively "shrink-wrapped" by the fibrous tissue in such a way as to form radial pockets in the fibrous tissue. These pockets contain the haptics with their outer ends positioned within the outer perimeter of the capsular bag. The lens is thereby fixated with the capsular bag with the lens optic aligned with the optical axis of the eye. The anterior capsule rim shrinks during fibrosis, and this shrinkage combined with the shrink-wrapping of the haptics causes some radial compression of the lens in a manner which tends to move the lens optic along the optical axis of the eye. The fibrosed, leather-like anterior capsule rim prevents anterior movement of the optic and urges the optic rearwardly during fibrosis. Accordingly, fibrosis induced movement of the optic occurs posteriorly to a distant vision position in which either (or both) the optic and inner ends of the haptics press rearwardly against the elastic posterior capsule wall, thereby stretching the posterior capsule wall rearwardly.

With time, depending on the rearward pressure of the intraocular lens on the posterior capsule wall as well as other factors (such as lens material, lens geometry, angulation, sharpness, wrinkles in the posterior capsule wall, etc), epithelium cells can migrate between the posterior capsule wall and the lens and reside and multiply in these spaces. Excessive build up of the cells in this area can lead to opacification of the optic. This opacification, commonly referred to as posterior capsule opacification (PCO), causes clouding of vision and can lead to blurring and possibly total vision loss. The process of PCO is slow and clinical changes often take one to two years to become apparent. PCO is typically treated by YAG laser capsulotomy. However, in terms of health economics, PCO is very expensive to treat.

Special care must also be taken that the material of the lens optic maintains transparency after it has been implanted within the eye and subject to ocular fluids. This characteristic is referred to herein as "in vivo transparency" or "in vivo transparent". Any significant clouding of the lens optic due to its interaction with ocular fluids can lead to blurring and possibly total vision loss in a manner similar to PCO. In U.S. Pat. No. 6,102,939, the inventor describes the crack resistance and biostability of a prosthesis implanted in vivo wherein the prosthesis formed from a polyolefinic copolymer material having a triblock polymer backbone comprising polystyrene-polyisobutylene-polystyrene, which is herein referred to as "SIBS", while also mentioning the desirability of long term elastomers for use in intraocular lenses as well as a long list of other applications (e.g., vascular grafts, endoluminal grafts, finger joints, indwelling catheters, pacemaker lead insulators, breast implants, hear valves, etc.). However, this patent fails to address important considerations (such as in vivo transparency) with regard to the suitability of the SIBS material for use in the ocular environment.

Modern intraocular lenses are made flexible where they can be folded in half to enable placement in the capsular bag through the scleral incision. However, such lenses typically have relatively lower indices of refraction, and thus such intraocular lenses are required to be thicker to provide the desired magnification characteristics of the intraocular lens. More particularly, the prior art foldable intraocular lenses are typically made of a silicone-based polymer with an index of refraction of 1.3 to 1.4, or made from an acrylic material with an index of refraction of 1.46. Such refractive indices are relatively low (for example, PMMA which is typically used for a rigid IOL has a refractive index of 1.49). Thus, such intraocular lenses are required to be thicker to provide the desired magnification characteristics of the intraocular lens. One skilled in the art understands that the magnification of a lens is dependent upon three values: i) radii of curvature; ii) index of refraction; and iii) thickness of the lens. Thus, for any given lens thickness, a greater index of refraction provides a greater degree of magnification. Alternatively, for any desired magnification, the higher the index of refraction enables the lens to be thinner. The thinner the lens, the smaller it can be folded or rolled. This allows the scleral incision to be made smaller and possibly avoids the use of sutures in closing the scleral incision. Suturing the scleral incision is disadvantageous because the scleral incision site, if not sutured properly, becomes a site of infection and leakage of aqueous fluid. Moreover, if the sutures are too lose or tight, astigmatism can form due to distortion of the cornea. On the other hand, if the scleral incision is small (e.g., less than a 2 mm slit), the incision will close on its own without the use of sutures. In addition, the thinner the lens, the more its radius of curvature can be deformed and/or axial displaced by changing tension in the anterior capsule by muscular contraction, thereby providing for enhanced accommodation after implantation.

Modern intraocular lens also act as a spectral filters that block out ultra-violet (UV) light that may burn the retina. Such UV light blocking capability is typically provided by additives that absorb UV radiation. Such additives are generally molecules that contain aromatic groups. These additives can migrate out of the polymeric material of the lens and cause toxic reactions.

Thus, there remains a need in the art to provide an intraocular lens device that is realized from a flexible biocompatible material that maintains in vivo transparency and has a relatively high index of refraction. Such features provide for a foldable intraocular lens that requires a small incision in the sclera, and thus provides for more effective healing of the eye as noted above. The relatively high index of refraction also provides for an intraocular lens with improved magnification capabilities.

There is also a need in the art to provide an intraocular lens device that is realized from a biocompatible material with ultra-violet light blocking capability that does not risk toxic reaction in the eye.

There is also need in the art to provide an intraocular lens device that inhibits epithelium cell migration and multiplication to thereby protect against PCO.

Several methods of manufacturing flexible, biocompatible intraocular lens devices are known, such as injection molding, spin casting, compression molding and transfer molding. These methods typically employ a polished stainless steel mold cavity that is formed in a geometry that achieves the desired curvature. Several significant problems have been associated with these molding techniques. One problem is that the stainless steel mold requires cleaning between molding cycles, which increases the labor costs and production costs associated with the finished product. Another problem is that steel molds typically have small gaps between the mold halves that allow "flash" to form in the gaps during the molding operation. Flash is unwanted material attached to the mold parting line on the finished product. This flash material must be removed from the finished product, which again increases the labor costs and production costs associated with the finished product.

Thus, there remains a need in the art to provide improved techniques for the manufacture of flexible, biocompatible intraocular lens devices which are less expensive than the prior art manufacturing techniques.

SUMMARY OF THE INVENTION

It is therefore an object of the invention to provide an ocular lens device that is realized from a flexible biocompatible material that maintains in vivo transparency and has a relatively high index of refraction.

It is another object of the present invention to provide such an ocular lens device that is suitable as an intraocular implant that requires a small incision in the sclera of the eye, and thus provide for more effective healing of the eye post-operatively as noted above.

It is a further object of the present invention to provide an ocular lens device that provides improved magnification capabilities.

It is yet another object of the present invention to provide an ocular lens device that is realized from a biocompatible material with ultra-violet light blocking capability that does not risk toxic reaction in the eye.

It is another object of the present invention to provide an intraocular lens device that inhibits epithelium cell migration and multiplication to thereby protect against PCO.

It is a further object of the present invention to provide a method (and corresponding apparatus) for the manufacture of the improved intraocular lens devices described herein.

It is yet another object of the present invention to provide a method (and corresponding apparatus) for the manufacture of intraocular lens devices which is less expensive than the prior art manufacturing techniques.

In accord with these objects, which will be discussed in detail below, an ocular lens device includes a refractive optics structure formed from a polyisobutylene-based material and a glassy segment. Preferably, the material has a central elastomeric polyolefinic block and thermoplastic end blocks (such as a triblock polymer backbone comprising polystyrene-polyisobutylene-polystyrene). The material of the refractive optics structure maintains in vivo transparency during implantation in its intended ocular environment for a substantial period of time. The material of the lens device is flexible such that it can be folded or rolled upon itself, which allows for the scleral incision to be made small (e.g., less than a 2 mm slit) and thus enables more effective healing of the scleral incision without sutures. The lens device preferably includes an optic portion and at least one haptic element that are adapted to rest within a capsular bag formed by a surgical procedure. The at least one haptic element supports the optic portion within the capsular bag. Preferably, the material of the refractive optics structure inherently blocks ultra-violet light without the addition of any additives.

According to one embodiment of the invention, the lens device may have a plurality of haptic elements that project radially away from the optic portion.

According to another embodiment of the invention, the lens device may have an annular haptic element that extends radially outward from the optic portion. The annular haptic element projects radially outward from the optic portion at an angle relative to the plane of the optic region at an angle between 0 and 45 degrees, and preferably at an angle between 10 and 20 degrees, and most preferably at an angle of 15 degrees. The optic portion preferably has a front convex surface and a flat back surface in addition to a stepped wall structure at its periphery.

According to yet another embodiment of the invention, the material of the lens device may be loaded with therapeutic drugs that interfere with cell proliferation, which is advantageous in intraocular applications in order to protect against PCO.

According to another embodiment of the invention, the in vivo transparent nature of the material of the refractive optics structure is accomplished by washing the polyisobutylene-based polymer to substantially remove remnant salts, and processing the polyisobutylene-based polymer at a controlled temperature(s) and/or a controlled processing time(s) to form a refractive optics structure. In one methodology, the refractive optics structure is formed by processing the polyisobutylene-based polymer material at controlled temperatures that are significantly less that the melting point of the polyisobutylene-based polymer. In another methodology, the refractive optics structure is formed by rapidly heating the polyisobutylene-based polymer to a temperature at or near its melting point, utilizing the resultant polymer melt to form the refractive optics structure in a closed mold, and then rapidly cooling the polymer/mold back to room temperature.

According to yet another embodiment of the invention, the lens device changes its radius of curvature or position in response to changes in tension of the lens capsule and/or from changes in pressure in the vitreous.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
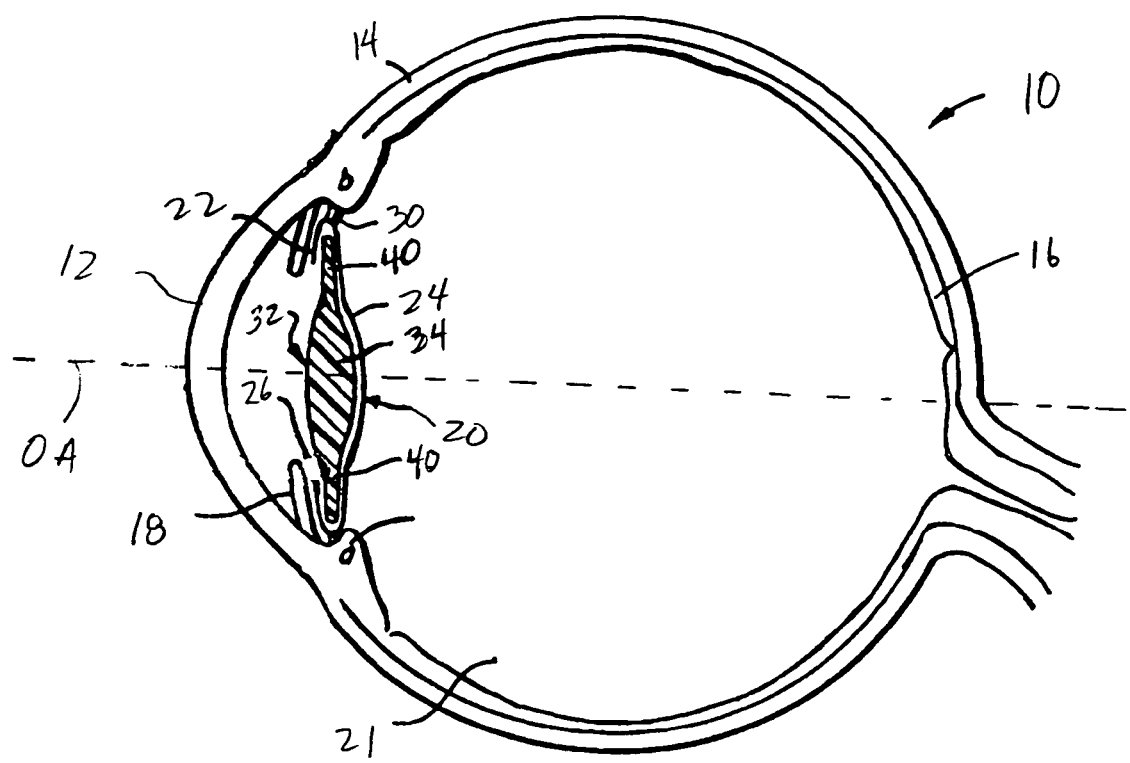
FIG. 1 is an illustration showing anatomic details of the human eye in addition to the implantation of an intraocular lens device in accordance with the present invention.

Turning now FIG. 1, there is shown a human eye 10 from which the natural crystalline lens matrix was previously removed by a surgical procedure involving an anterior capsulotomy, in this case a continuous tear circular tear capsulotomy, or capsulorhexis. The natural lens comprises a lens capsule having elastic anterior and posterior walls, which are referred herein as anterior and posterior capsules, respectively. As mentioned earlier, continuous tear circular capsulotomy, or capsulorhexis, involves making an incision in the sclera of the eye. Tooling is inserted through this incision and manipulated to tear the anterior capsule along a generally circular tear line in such a way as to form a relatively smooth-edged circular opening in the center of the anterior capsule. The cataract is removed from the natural lens capsule through the scleral incision. After completion of this surgical procedure, the eye includes an optically clear anterior cornea 12, an opaque sclera 14, a retina 16, an iris 18, a capsular bag 20 behind the iris, and a vitreous cavity 21 behind the capsular bag filled with the gel-like vitreous humor. The capsular bag 20 is the structure of the natural lens of the eye which remains intact after the capsulorhexis has been performed and the natural lens matrix has been removed. The capsular bag 20 includes an annular anterior capsular remnant or rim 22 and an elastic posterior capsule 24 which are joined along the perimeter of the bag 20 to form an annular crevice-like bag structure between the capsular rim 22 and posterior capsule 24. The capsular rim 22 is the remnant of the anterior capsule of the natural lens which remains after capsulorhexis has been performed on the natural lens. This rim circumferentially surrounds a central, generally round anterior opening 26 (capsulotomy) in the capsular bag through which the natural lens matrix was previously removed from the natural lens. The capsular bag 20 is secured about its perimeter to the ciliary muscle of the eye by zonules 30. Eye 10 also includes an optical axis OA-OA that is an imaginary line that passes through the optical center of intraocular lens 32. An optical axis OA in the human eye 10 is generally perpendicular to a portion of cornea, natural lens and retina.

Natural accommodation in a normal human eye involves contraction and relaxation of the ciliary muscle of the eye by the brain in response to looking at objects at different distances. Ciliary muscle relaxation, which is the normal state of the muscle, positions and shapes the human crystalline lens for distant vision. Ciliary muscle contraction positions and shapes the human crystalline lens for near vision. The brain-induced change from distant vision to near vision is referred to as accommodation.

Figure 2:
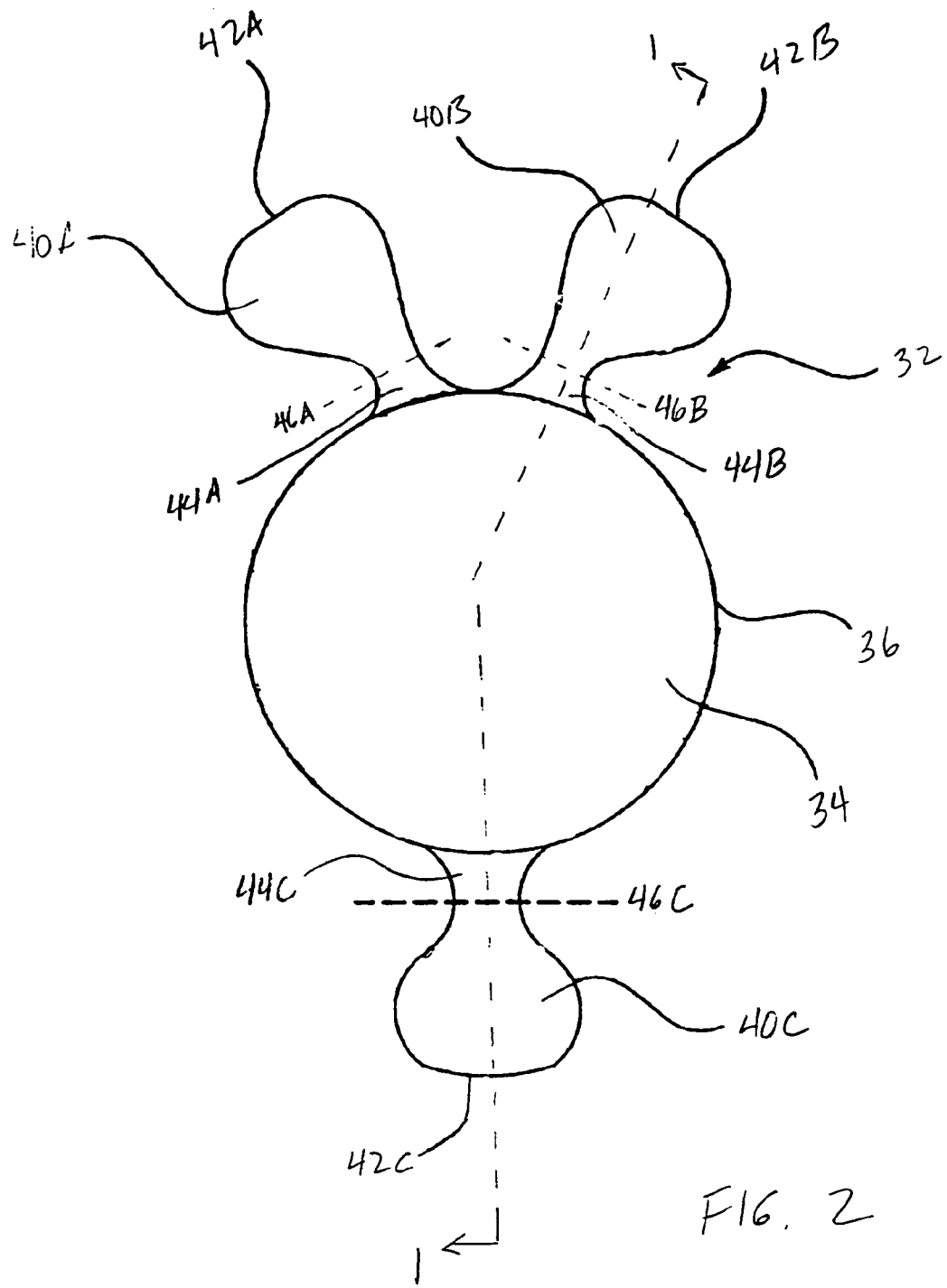
FIG. 2 is a front view of an exemplary embodiment of an intraocular lens device in accordance with the present invention.

An accommodating intraocular lens 32 according to the present invention is implanted through the scleral incision into the capsular bag 20 of the eye 10. The intraocular lens 32 replaces and performs the accommodation function of the removed natural crystalline lens. As illustrated in FIG. 2, the intraocular lens 32 of the present invention includes an optic portion 34 with an outer peripheral edge 36. Three haptic elements 40A, 40B, 40C (collectively, 40) project radially outward from the peripheral edge 36 of optic portion 34. The haptic elements 40A, 40B, 40C are preferably integrally formed with and permanently connected to the outer peripheral edge 36 of optic portion 34. The haptic elements 40A, 40B, 40C include respective end portions 42A, 42B, 42C that are adapted to rest in and engage the annular capsular bag 20, which is disposed between the capsular rim 22 and posterior capsule 24. The end portions 42A, 42B, 42C are held in place through compressive forces exerted by the inner surfaces of the capsular bag 20 thereon. In this position, the optic portion 34 is substantially aligned with the optical axis OA of the eye, the posterior side of the optical portion 34 faces the elastic posterior capsule 24, and the end portions 42A, 42B, 42C fit snuggly within the capsular bag 20 at the radially outer perimeter of the bag, which prevents decentration of the intraocular lens 32.

The haptic elements 40A, 40B, 40C also include hinge portions 44A, 44B, 44C which join the end portions of the haptic elements to the optic portion 34. The haptic elements 40A, 40B, 40C are flexible about the respective hinge portions 44A, 44B, and 44C anteriorly and posteriorly relative to the optic portion 34. The hinge portions 44A, 44B, 44C may be formed by narrowing structures as shown. Alternatively, the hinged portions may be formed by grooves or other structural features of the haptic elements 40A, 40B, and 40C. In this manner, the haptic elements 40A, 40B, 40C are adapted to flex about respective axes 46A, 46B, 46C such that the optic portion 34 moves generally along the optical axis OA of eye 10, thereby achieving axial displacement of the optic portion 34 in a direction along optical axis OA. By designing such flexion characteristic into the haptic elements 40A, 40B, 40C, the intraocular lens 32 allows an eye to achieve multifocal visual imaging without the aid of eyeglasses.

In alternate embodiments, the haptic elements 40 are adapted to transmit radial forces applied to rim of capsular bag by ciliary muscle contraction and relaxation to the optic portion 34, whose radius of curvature (e.g., diopter) changes in response thereto. In such embodiments, the haptic elements 40 are preferably adapted such that the optic portion 34 is not substantially displaced along the optical axis OA of eye 10 in response to such ciliary muscle contraction and relation. By designing such deformation characteristics into the haptic elements 40 and the optic portion 34, the intraocular lens 32 allows the eye to achieve multifocal visual imaging without the aid of eyeglasses.

According to the preferred embodiment of the present invention, the intraocular lens 32 (or a portion of the lens 32 such as the optic portion 34) is formed from a polyolefinic copolymer material having a triblock polymer backbone comprising polystyrene-polyisobutylene-polystyrene, which is herein referred to as "SIBS". Non-cross linked high molecular weight polyisobutylene (PIB) is a soft putty-like material with a Shore hardness less than 20A. When copolymerized with polystyrene, it can be made at hardnesses ranging up to the hardness of polystyrene, which has a Shore hardness of 100D. Thus, depending on the relative amounts of styrene and isobutylene, the SIBS material can have a range of hardnesses from as soft as Shore 10A to as hard as Shore 100D. In this manner, the SIBS material can be adapted to have the desired elastomeric and hardness qualities. In the preferred embodiment, the SIBS material for lens 32 (including the optic portion 34 and the haptic elements) is flexible such that it can be folded and/or rolled upon itself, which minimizes the size of the scleral incision required for implantation and enables healing of the scleral incision without sutures. It therefore provides for more effective healing of the eye post-operatively as noted above. After inserting the lens 32 in its folded state through the scleral incision, the lens 32 is unfolded and positioned such that it is supported within the capsulary bag. The optic portion 34 and the haptic elements can be realized from the same SIBS material, a different SIBS material (e.g., a SIBS material with a different hardness quality), or from different biocompatible polymers altogether. When formed from different materials, the haptic elements can be insert-molded, adhered with an adhesive or heat or sonic welded to the optics portion 34 of the lens 32. Details of the SIBS material is set forth in U.S. Pat. Nos. 5,741,331; 6,102,939; 6,197,240; 6,545,097, which are hereby incorporated by reference in their entirety.

The SIBS material of the intraocular lens 32 may be polymerized under control means using carbocationic polymerization techniques such as those described in U.S. Pat. Nos. 4,276,394; 4,316,973; 4,342,849; 4,910,321; 4,929,683; 4,946,899; 5,066,730; 5,122,572; and Re 34,640, each herein incorporated by reference in its entirety. The amount of styrene in the copolymer material is preferably between about 1 mole percent to 30 mole %. The styrene and isobutylene copolymer materials are preferably copolymerized in solvents.

In accord with another aspect of the invention, it is expected that alternative polymeric materials are suitable for the practice of the present invention. Such alternative polymeric materials preferably include polyisobutylene-based material capped with a glassy segment. The glassy segment provides hard domains for the elastomeric polyisobutylene and is non-reactive in the ocular environment (e.g., it will not react with the fluid of the eye). The glassy segment preferably does not contain any cleavable group which will release in the presence of body fluid inside the human eye and cause toxic side effects. Moreover, the polyisobutylene-based material and glassy segment preferably avoid cell encapsulation in the ocular environment. The glassy segment can be a vinyl aromatic polymer (such as polystyrene, α-methylstyrene, or a mixture thereof), or a methacrylate polymer (such as methylmethacrylate, ethylmethacrylate, hydroxymethalcrylate, or a mixture thereof). Such materials preferably have a general block structure with a central elastomeric polyolefinic block and thermoplastic end blocks. Even more preferably, such materials have a general structure:

BAB or ABA (linear triblock), $B(AB)_n$ or $A(BA)_n$ (linear alternating block), or $X-(AB)_n$ or $X-(BA)_n$ (includes diblock, triblock and other radial block copolymers), where A is an elastomeric polyolefinic block, B is a thermoplastic block, n is a positive whole number and X is a starting seed molecule.

Such materials may be star-shaped block copolymers (where n=3 or more) or multi-dendrite-shaped block copolymers.

During a post-operative healing period on the order of two to three weeks following surgical implantation of the lens 32 in the capsular bag 20, epithelial cells cause fusion of the inner surface of the rim 22 to the posterior capsule 24 by fibrosis. In the case that the haptic elements 40A, 40B, 40C are formed from a material that avoids cell encapsulation in the ocular environment, the non-encapsulating nature of the material causes the fibrosis to occur around the haptic elements 40A, 40B, 40C in such a way that the haptic elements are loosely wrapped by the capsular bag 20 to form pockets in the fibrosed material. These pockets cooperate with the haptic elements 40A, 40B, 40C to position and center the lens 32 in the eye. Ciliary muscle induced flexing of the lens 32 during fibrosis can be resisted or prevented by using a cyclopegic and/or by wrapping sutures around the hinge portions 44A, 44B, 44C. Removal of these sutures after completion of fibrosis may be accomplished by using sutures that are either absorbable in the fluid within the eye or by using sutures made of a material, such as nylon, which can be removed by a laser.

Figure 3:
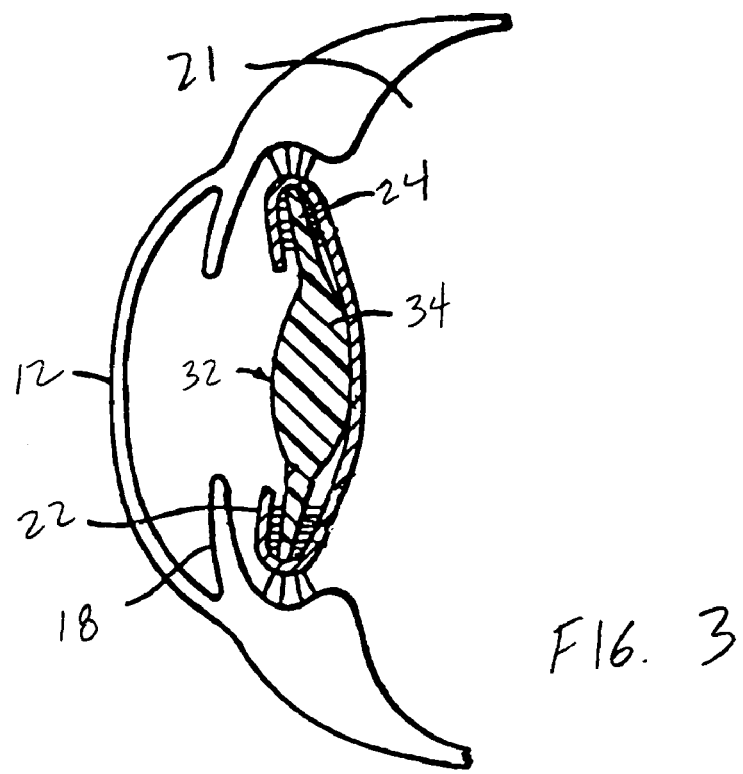
FIGS. 3 and 4 illustrate the operation of the intraocular lens device of FIG. 2 to provide for accommodation of the eye in response to contraction and relaxation of the ciliary muscles of the eye.
Figure 4:
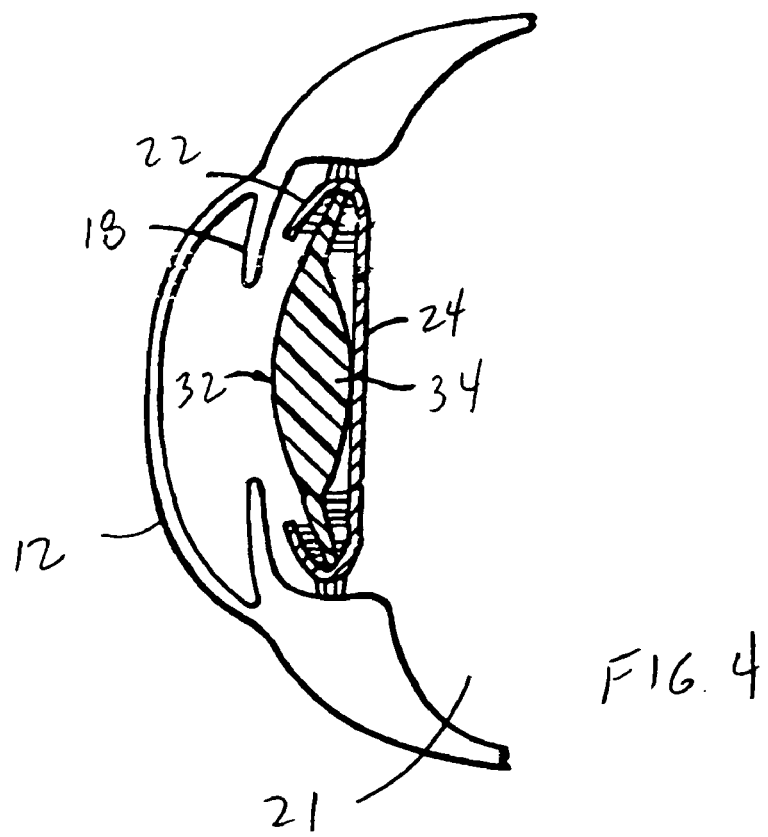

Natural accommodation in a normal human eye involves shaping of the natural crystalline lens by automatic contraction and relaxation of the ciliary muscle of the eye by the brain to focus the eye at different distances. Ciliary muscle relaxation shapes the natural lens for distant vision. Ciliary muscle contraction shapes the natural lens for near vision. The accommodating intraocular lens 32 is adapted to utilize this same ciliary muscle action, the fibrosed capsular rim 22, the elastic posterior capsule 24, and the vitreous pressure within the vitreous cavity 21 to effect accommodation movement of the lens optic 34 along the optic axis of the eye between its distant vision position of FIG. 3 to its near vision position of FIG. 4. Thus, when looking at a distant scene, the brain relaxes the ciliary muscles. Relaxation of the ciliary muscles stretches the capsular bag 20 to its maximum diameter and its fibrosed anterior rim 22 to the taut trampoline-like condition or position discussed above. The taut rim deflects the optics portion 34 rearwardly to its posterior distant vision position of FIG. 3 in which the elastic posterior capsule 24 is stretched rearwardly by the optics portion 34 and thereby exerts a forward biasing force on the lens 32. When looking at a near scene, such as a book when reading, the brain constricts or contracts the ciliary muscle. This ciliary muscle contraction increases the vitreous cavity pressure and relaxes the capsular bag 20 and particularly its fibrosed capsular rim 22. The relaxed capsular bag 20 exerts opposing endwise compression forces on the ends of the haptic elements 40A, 40B, and 40C with resultant endwise compression of the lens 32. Such relaxation of the capsular rim permits the rim to flex forwardly and thereby enables the combined forward bias force exerted on the lens by the rearwardly stretched posterior capsule and the increased vitreous cavity pressure to push the lens forwardly to its near vision position of FIG. 4. Intermediate vision positions between the far vision position of FIG. 3 and the near vision position of FIG. 4 are obtained by relaxation and/or contraction of the ciliary muscles in a manner similar to that described above, which allows the eye to focus at different distances.

Figure 9A:
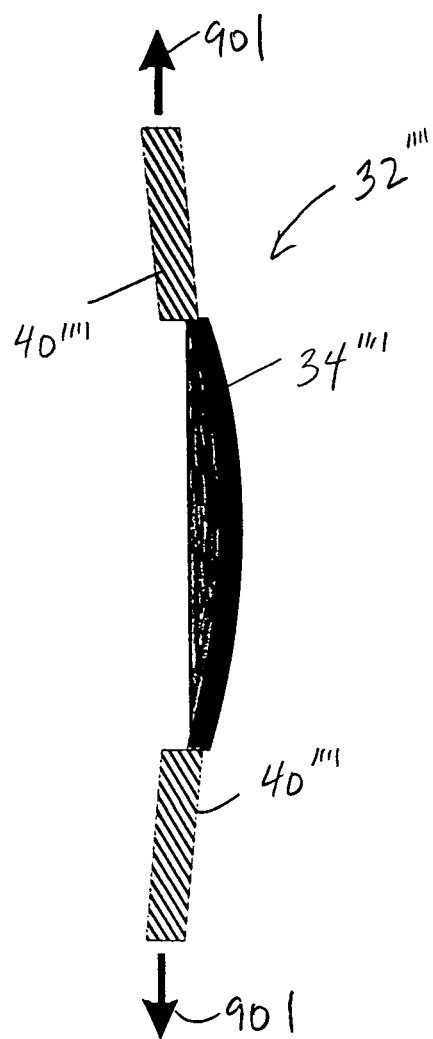
FIGS. 9A and 9B illustrate the operation of an alternate embodiment of intraocular lens device in accordance with the present invention in providing for accommodation of the eye in response to contraction and relaxation of the ciliary muscles of the eye.
Figure 9B:
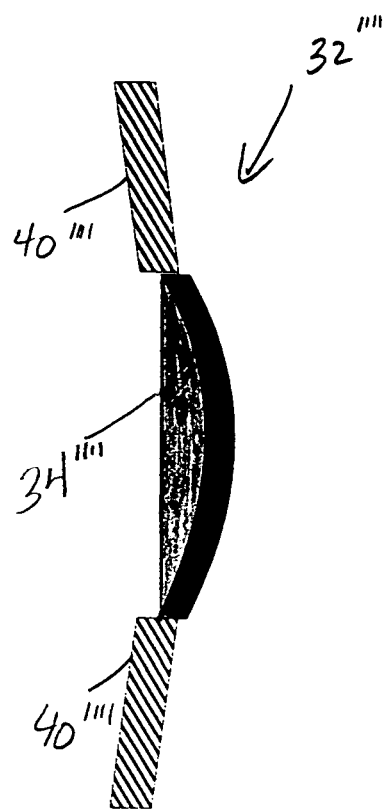

In alternate embodiments, such as those described below with respect to FIGS. 9A and 9B, accommodation is provided by changing the radius of curvature of the optic portion of the lens without substantially changing the position of the lens device along the optical axis (OA) of the eye. In these embodiments, relaxation of the ciliary muscles (which is accomplished by the brain when looking at a distant scene) stretches the capsular bag 20 and its fibrosed anterior rim 22 to the taut trampoline-like condition or position discussed above. The taut rim applies radial tension to the haptic elements 40 and optics portion 34 of the lens device 32, which causes the radius of curvature of the optic portion 34 to increase (FIG. 9A). When looking at a near scene, the brain constricts or contracts the ciliary muscle. This ciliary muscle contraction increases the vitreous cavity pressure and relaxes the capsular bag 20 and particularly its fibrosed capsular rim 22. The relaxed capsular bag 20 releases the radial forces on the haptic elements 40 and the optic portion 34 of the lens device 32 such that the radius of curvature of the optic portion 34 decreases (FIG. 9B). These operations provide for accommodation which allows the eye to focus at different distances.

Figure 5:
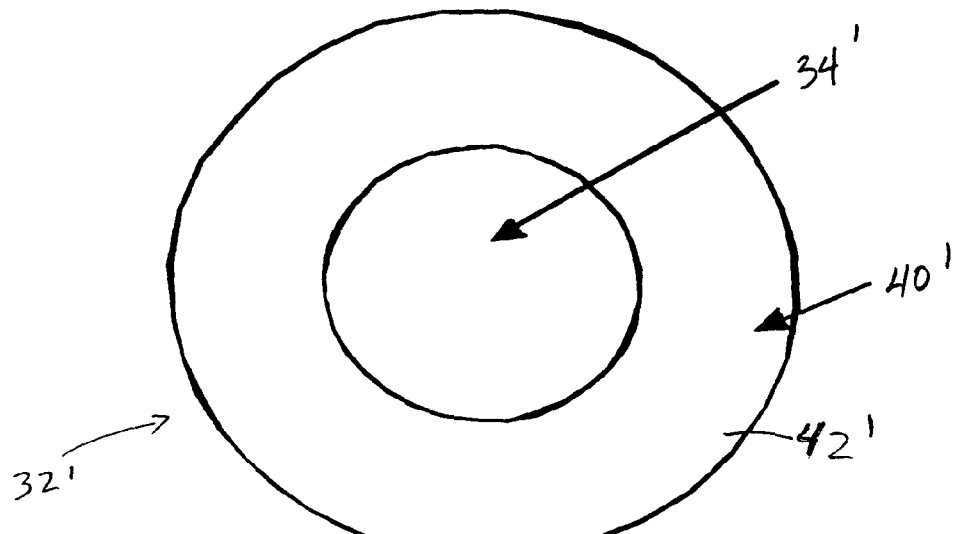
FIG. 5 is a front view of an alternate embodiment of an intraocular lens device in accordance with the present invention.
Figure 6A:
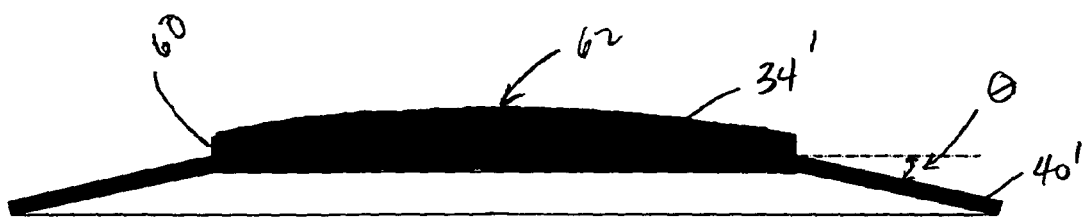
FIGS. 6A, 6B and 6C illustrate different annular haptic designs that can be utilized in the embodiment of FIG. 5.
Figure 6B:
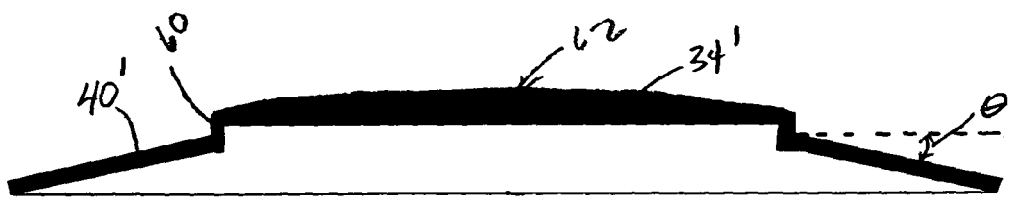
Figure 6C:

The IOL of the present invention can also be realized by different haptic designs, such as those that utilize two haptics, four haptics, and ring haptics as is well known in the art. FIG. 5 illustrates a top view of an IOL 32' with an optic portion 34' and an annular haptic element 40'. Cross-sections for different embodiments are shown in FIGS. 6A-6C. The front and back surfaces of optic portion 34' can be of any diopter (curvature) necessary to provide the desired correction for the patient. For example, the front surface of the optic portion 34' may be convex as shown in FIGS. 6A-C or possibly concave (not shown). The back surface of the optic portion 34' is preferably flat as shown in FIGS. 6A-6C, but it may be concave or convex to add or subtract magnification.

As shown in FIGS. 6A-6C, the angle θ of the annulus of the haptic element 40' relative to the plane of the optic portion 34' (which is disposed substantially perpendicular to the optical axis of the eye) is between 0 and 45 degrees, and more preferably between 10 and 20 degrees, and most preferably 15 degrees. The IOL 34' is formed from a flexible material, such as the SIBS material described above, such that it can be folded and/or rolled upon itself, which minimizes the size of the scleral incision required for implantation and enables healing of the scleral incision without sutures. It therefore provides for more effective healing of the eye post-operatively as noted above. After inserting the IOL 34' in its folded state through the scleral incision, the IOL 34' is unfolded and positioned such that it is supported within the capsulary bag. When placed in the capsular bag, the annular haptic element 40' is adapted to rest in and engage the annular capsular bag 20, which is disposed between the capsular rim 22 and posterior capsule 24. The peripheral portion 42' of the annular haptic element 40' is held in place through compressive forces exerted by the inner surfaces of the capsular bag 20 thereon. In this position, the optic portion 34' is substantially aligned with the optical axis OA of the eye, the posterior side of the optical portion 34' faces the elastic posterior capsule 24, and the peripheral portion 42' of the annular haptic element 40' fits snuggly within the capsular bag 20 at the radially outer perimeter of the bag, which prevents decentration of the intraocular lens 32'. This configuration is similar to the configuration shown in FIG. 1.

As shown in FIGS. 6A and 6B, the outer edge of the optic portion 34' may be defined by a step 60, which serves as a boundary wall to prevent cells from migrating from the periphery of the lens 32' and over the area of the optic portion 34'. Note however that the step 60 may be omitted as shown in the embodiment of FIG. 6C, especially if antiproliferating or antimigration agents are used to prevent cell multiplication and migration under the lens.

The embodiment of FIG. 6B is similar to the embodiment of FIG. 6A, except that the thickness (i.e., the distance between front and back surfaces) of the optic portion 34' is smaller in the embodiment of FIG. 6B, which should allow the optic portion 34' to be folded or rolled smaller. In addition, the flat surface of the lens can be curved to provide more magnification if desired. Alternate embodiments with annular haptic designs are shown in FIGS. 7 and 8.

Figure 7:
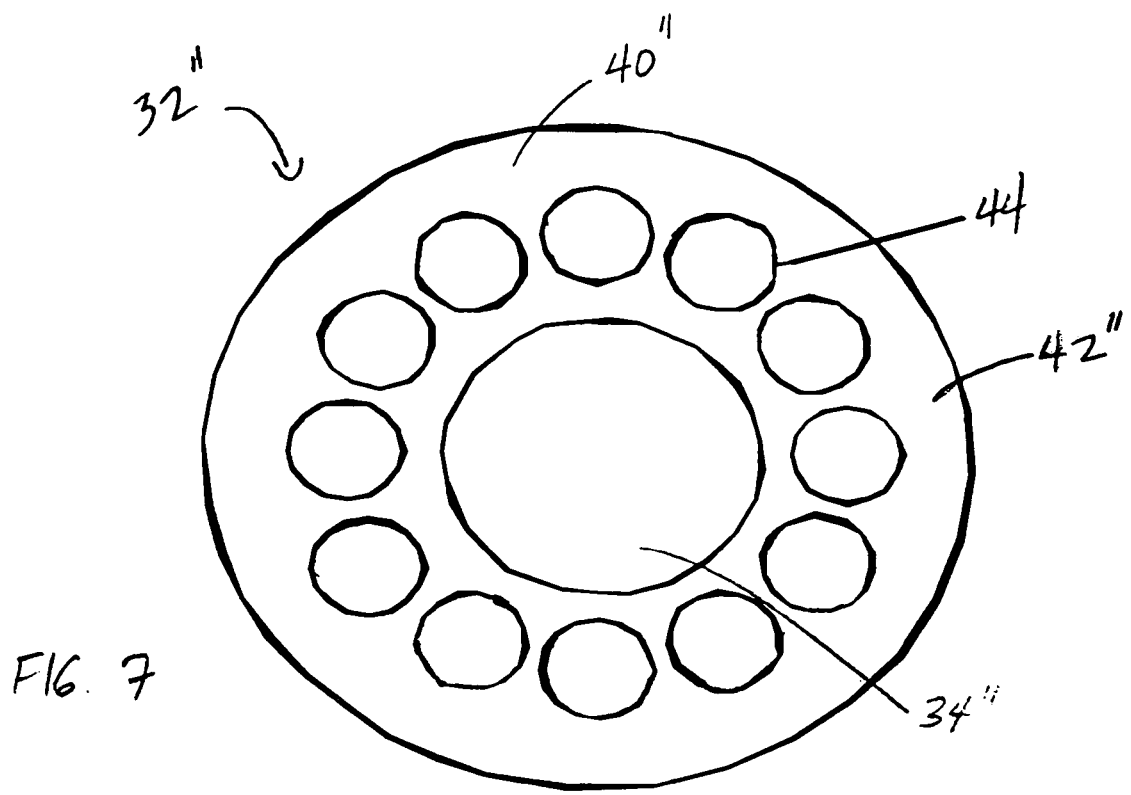
FIGS. 7 and 8 are front views of alternate embodiments of an intraocular lens device in accordance with the present invention.

In the embodiment of FIG. 7, a plurality of holes 44 are formed about the annular haptic 40". These holes preferably enable fluid or viscoelastic (if used) migration between the front and back of the lens 32" as well as aid in fixation of the lens to the annular capsular bag by cellular ingrowth. More particularly, during a post-operative healing period on the order of two to three weeks following surgical implantation of the lens 32" in the capsular bag 20, epithelial cells cause fusion of the inner surface of the rim 22 to the posterior capsule 24 by fibrosis. In the case that the annular haptic element 40" is formed from the SIBS material, the non-encapsulating nature of the SIBS material causes the fibrosis to occur through the holes 44 in such a way that the haptic element 40" is wrapped tightly by the capsular bag. Ciliary muscle induced flexing of the lens 32" during fibrosis can be resisted or prevented by using a cyclopegic and/or by other means.

Figure 8:
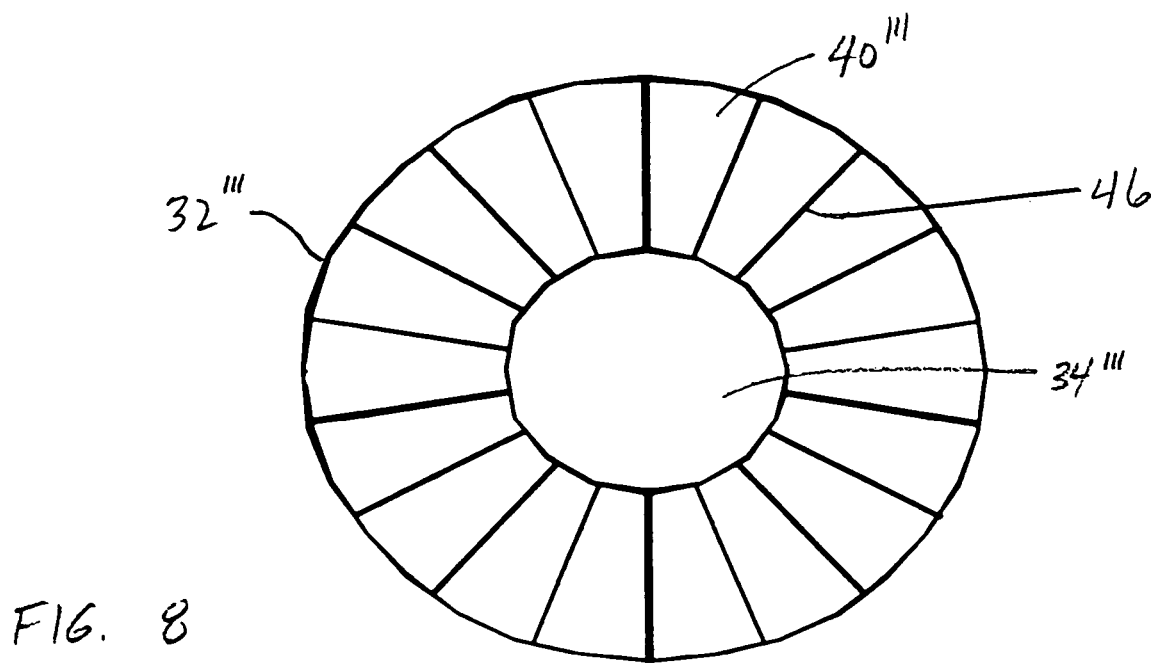

In the embodiment of FIG. 8, the annular haptic element 40'" has a plurality of radial cuts 46 formed therein. The radial cuts 46 extend radially from the central optic portion 34'" to the periphery of the annular haptic element 40'" as shown. The radial cuts 46 better enable proper placement into the capsular bag.

In the embodiments of FIGS. 5-8, the circular nature of the haptic annulus helps force the lens against the posterior capsule 24 and helps prevent wrinkles from forming in the capsule and channels for cell migration (which can lead to PCO). In addition, the force of the annular haptic element against the lens capsule is such that ciliary muscle contraction and relaxation causes movement of the optic region along the optical axis by puckering of the lens (in other words, changing the angle _). In this manner, the annular haptic provides for accommodation between a far vision position and near vision position in a manner similar to that described above with respect to FIGS. 3 and 4, and thus allows the eye to focus at different distances without the need for reading glasses. Alternatively, the annular haptic element can be adapted such that ciliary muscle contraction and relaxation causes the optic portion of the lens to bow and change its radius of curvature as shown in FIGS. 9A and 9B.

In another embodiment shown in FIGS. 9A and 9B, an accommodating lens device 32"" is shown having an optic portion 34"" and haptic elements 40"" wherein the thickness of the haptic elements 40"" is greater than the thickness of the optic portion 34"". Alternatively, the modulus of elasticity of the material of haptic elements 40"" may be greater than the modulus of elasticity of the material of the optic portion 34"". In this configuration, when tension is applied radially, as depicted by the arrows 901 of FIG. 9A, the radius of curvature of the optic portion 34"" increases. When the tension is released, the optic portion 34"" reverts back to its natural state with a smaller radius of curvature as shown in FIG. 9B. Such operations provide for change in diopter of the optic portion 34"" and accommodation of the lens device. By forming the optic portion 34"" with a smaller thickness (or smaller modulus of elasticity) that the haptic elements 40"", the response (e.g., change in diopter) of the optic portion 34"" to the radial tension forces applied thereto is maximized, which allows for a greater range of accommodation of the eye. The smaller thickness optic portion 34"" may also allow for the scleral incision to be made smaller and thus provide for more effective healing of the eye post-operatively as noted above.

It was surprisingly found that the polyisobutylene-based material of the intraocular lens 32 as described herein has a high index of refraction ranging from 1.52 to 1.54. This relatively high index of refraction provides for improved magnification capabilities, and also allows the lens 23 to be thinner for a given magnification factor. Decreasing the thickness of the lens 23 is advantageous because it allows the scleral incision to be made smaller and thus provide for more effective healing of the eye post-operatively as noted above. It also provides for improved response to ciliary muscle contraction and relaxation as noted above.

It was also surprisingly found that the SIBS material of the intraocular lens 32 effectively blocks ultra-violet light. More particularly, the aromatic styrene groups of the polystyrene-polyisobutylene-polystyrene SIBS material are natural intrinsic filters of ultra-violet light. Thus, the exemplary SIBS material of the intraocular lens 32 may advantageously block ultra-violet light without the need for potentially toxic additives.

The polymeric intraocular lens 32 of the present invention can be loaded with therapeutic drugs that release over time and interfere with the ability of the epithelial cells of the eye to migrate and reproduce, and thereby protect against PCO. It is expected that the amount of drug required for this therapy will be in the picogram to microgram range. The therapeutic drugs loaded into the intraocular lens can include cytostatic agents (i.e., antiproliferation agents that prevent or delay cell division, for example, by inhibiting replication of DNA or by inhibiting spindle fiber formation, and/or inhibit the migration of cells into the posterior space).

Representative examples of cytostatic agents include the following:
- modified toxins;
- methotrexate;
- adriamycin
- radionuclides (e.g., such as disclosed in U.S. Pat. No. 4,897,255, herein incorporated by reference in it entirety);
- protein kinase inhibitors, including staurosporin (which is a protein kinase C inhibitor) as well as a diindoloalkaloids and stimulators of the production or activation of TGF-beta, including tamoxifen and derivatives of functional equivalents (e.g., plasmin, heparin, compounds capable of reducing the level or inactivating the lipoprotein Lp(a) or the glycoprotein apolipoprotein(a) thereof)
- nitric oxide releasing compounds (e.g., nitroglycerin) or analogs or functional equivalents thereof;
- paclitaxel or analogs or functional equivalents thereof (e.g., taxotere), for example an agent based on Taxol® (whose active ingredient is paclitaxel);
- inhibitors of specific enzymes (such as the nuclear enzyme DNA topoisomerase II and DAN polymerase, RNA polyermase, adenl guanyl cyclase);
- superoxide dismutase inhibitors;
- terminal deoxynucleotidyl-transferas;
- reverse transcriptase;
- antisense oligonucleotides that suppress smooth muscle cell proliferation;
- angiogenesis inhibitors (e.g., endostatin, angiostatin and squalamine);
- rapamycin;
- cerivastatin; and
- flavopiridol and suramin and the like.

Other examples of cytostatic agents include the following:
- peptidic or mimetic inhibitors (i.e., antagonists, agonists, or competitive or non-competitive inhibitors) of cellular factors that may (e.g., ion the presence of extracellular matrix) trigger proliferation of cells or pericytes (e.g., cytokines (for example, interleukins such as IL-1), growth factors (for example, PDGF, TGF-alpha or -beta, tumor necrosis factor, smooth muscle- and endothelioal-derived growth factors such as endothelin or FGF), homing receptors (for example, for platelets or leukocytes), and extracellular matrix receptors (for example, integrins).

Representative examples of useful therapeutic agents in the category of agents that address cell proliferation include:
- subfragments of heparin;
- triazolopyrimidine (for example, trapidil, which is a PDGF antagonist);
- lovastatin; and
- prostaglandins E1 or I2.

Representative examples of therapeutic agents that inhibit migration of cells into the posterior space include the following:
- agents derived from phenylalanine (for example cytochalasins), tryptophan (for example (chetogobosins), or luecine (for example, asphalasins, resulting in a benzyl, indol-3-yl methyl or isobutyl group, respectively, at position C-3 of a substituted perhydroisoindole-1-one moiety.

Several of the above and numerous additional therapeutic agents appropriate for the practice of the present invention are disclosed in U.S. Pat. Nos. 5,733,925 and 6,545,097, both of which are herein incorporated by reference in their entirety.

If desired, a therapeutic agent of interest can be provided at the same time as the copolymer, for example, by adding it to a copolymer melt during thermoplastic processing or by adding it to a copolymer solution during solvent-based processing. The therapeutic agent can be added to the optics portion or to the haptic elements or to both the optics portion and the haptic elements of the lens device.

Alternatively, a therapeutic agent can be provided after formation of the device or device portion. As an example of these embodiments, the therapeutic agent can be dissolved in a solvent that is compatible with both the copolymer and the therapeutic agent. Preferably, the lens copolymer is at most only slightly soluble in the solvent. Subsequently, the solution is contacted with the device or device portion such that the therapeutic agent is loaded (e.g., by leaching/diffusion) into the copolymer. For this purpose, the device or device portion can be immersed or dipped into the solution, the solution can be applied to the device or component, for example, by spraying, printing dip coating, immersing in a fluidized bed and so forth. The device or component can subsequently be dried, with the therapeutic agent remaining therein.

In another alternative, the therapeutic agent may be provided within a matrix comprising the copolymer of the intraocular lens. The therapeutic agent can also be covalently bonded, hydrogen bonded, or electrostatically bound to the copolymer. As specific examples, nitric oxide releasing functional groups such as S-nitroso-thiols can be provided in connection with the copolymer, or the copolymer can be provided with charged functional groups to attach therapeutic groups with oppositely charged functionalities.

In yet another alternative embodiment, the therapeutic agent can be precipitated onto the surface of a lens device or lens device portion. This surface can be subsequently covered with a coating of copolymer (with or without additional therapeutic agent) as described above.

Hence, when it is stated herein that the copolymer is "loaded" with therapeutic agent, it is meant that the therapeutic agent is associated with the copolymer in a fashion like those discussed above or in a related fashion.

In some instances a binder may be useful for adhesion to a substrate. Examples of materials appropriate for binders in connection with the present invention include silanes, titanates, isocyanates, carboxyls, amides, amines, acrylates hydroxyls, and epoxides, including specific polymers such as EVA, polyisobutylene, natural rubbers, polyurethanes, siloxane coupling agents, ethylene and propylene oxides.

It also may be useful to coat the copolymer of the lens (which may or may not contain a therapeutic agent) with a layer with an additional polymer layer (which may or may not contain a therapeutic agent). This layer may serve, for example, as a boundary layer to retard diffusion of the therapeutic agent and prevent a burst phenomenon whereby much of the agent is released immediately upon exposure of the lens device or device portion to the implant site. The material constituting the coating, or boundary layer, may or may not be the same copolymer as the loaded copolymer.

For example, the barrier layer may also be a polymer or small molecule from the following classes: polycarboxylic acids, including polyacrylic acid; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA (ethylene-vinyl acetate copolymer); polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; polypeptides, including proteins; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.); fibrin; collagen and derivatives thereof; polysaccharides such as celluloses, starches, dextrans, alginates and derivatives; and hyaluronic acid. Copolymers and mixtures of the above are also contemplated.

It is also possible to form the lens device (or lens device portion) with blends by adding one or more of the above or other polymers to a block copolymer. Examples include the following:

- blends can be formed with homopolymers that are miscible with one of the block copolymer phases. For example, polyphenylene oxide is miscible with the styrene blocks of polystyrene-polyisobutylene-polystyrene copolymer. This should increase the strength of a molded part or coating made from polystyrene-polyisobutylene-polystyrene copolymer and polyphenylene oxide.
- blends can be made with added polymers or other copolymers that are not completely miscible with the blocks of the block copolymer. The added polymer or copolymer may be advantageous, for example, in that it is compatible with another therapeutic agent, or it may alter the release rate of the therapeutic agent from the block copolymer (e.g., polystyrene-polyisobutylene-polystyrene copolymer).
- blends can be made with a component such as sugar (see list above) that can be leached from the device or device portion, rendering the device or device component more porous and controlling the release rate through the porous structure.

The release rate of therapeutic agent from the therapeutic-agent-loaded block copolymers of the present invention can be varied in a number of ways. Examples include:

- varying the molecular weight of the block copolymers;
- varying the specific constituents selected for the elastomeric and thermoplastic portions of the block copolymers and the relative amounts of these constituents;
- varying the type and relative amounts of solvents used in processing the block copolymers;
- varying the porosity of the block copolymers;
- providing a boundary layer over the block copolymer; and
- blending the block copolymer with other polymers or copolymers.

Moreover, although it is seemingly desirable to provide control over the release of the therapeutic agent (e.g., as a fast release (hours) or as a slow release (weeks)), it may not be necessary to control the release of the therapeutic agent. In such embodiments, one or more of the therapeutic drug agents described herein (e.g., an antiproliferative agent derived from paclitaxyl) may be injected into the lens capsule at the time of surgery. In this case, the agent "sterilizes" the tissue cells that cause PCO within the short time it exists in the eye, and it can be delivered neat (without a carrier) at the time of surgery.

For ocular applications, it is desirable that the material of at least the optic of the ocular lens device maintain in vivo transparency for substantial periods of time. As used herein, "in vivo transparency" or "transparent" shall mean that the material transmits at least 80% of the light incident thereon in the visible range (e.g., between 400 and 700 nm of the electromagnetic spectrum). It was found that a film of SIBS material formed by traditional thermal processing techniques (e.g., injection molding, compression molding, or extrusion at temperatures at or near the melting point of the SIBS material and then slow cooled to cure the polymer) is transparent in air; however, the film begins to cloud and become opaque with time when equilibrated in water, saline or other aqueous bodily fluids (collectively referred to below as "water"). Further, the extent of such clouding increases as the water is heated. At temperatures near the boiling point of water, the SIBS film becomes totally white-opaque and can absorb as much as 10% of its weight in water. Considering that the SIBS material is comprised of polyisobutylene and polystyrene, which are both hydrophobic material, this result is surprising.

In accord with the present invention, the polyisobutylene-based material of at least the optic of the ocular lens devices described herein is adapted to maintain in vivo transparency for substantial periods of time. Generally, this is accomplished by satisfying the following two steps: 1) washing remnant salts and other unwanted chemicals from the polyisobutylene-based material; and 2) processing the washed polyisobutylene-based material at a controlled temperature(s) and/or a controlled processing time(s) to form the optic and possibly other parts of the ocular lens devices described herein. In one methodology, the optic (and possibly other parts of the ocular lens device) is formed by processing the polyisobutylene-based polymer material at controlled temperatures that are significantly less that the melting point of the polyisobutylene-based polymer. In another methodology, the optic (and possibly other parts of the ocular lens device) is formed by rapidly heating the polyisobutylene-based polymer to a temperature at or near its melting point. The resultant polymer melt is added to a mold that forms the optic (and possibly other parts of the ocular lens device). The polymer and mold is quickly cooled back to room temperature for removal of the optic. In addition, optical clarity additives may be added to the polyisobutylene-based material to help in this regard; however, it is not always desirous to use these additives as they may leach from the polymer and into the ocular environment and provoke an undesirable response.

The polyisobutylene-based material is typically synthesized in organic solvent using a Lewis acid as an initiator. One such Lewis acid that is preferred for this application is titanium tetrachloride. In order to quench the reaction, chemicals such as alcohols (methanol, for example) are added in excess to the reaction stoicheometry which immediately quenches the reaction by neutralizing titanium tetrachloride. At completion of the reaction, titanium tetrachloride is converted into various salts of titanium, including titanium dioxide, titanium methoxide, and the like. In addition, depending upon the reaction vessel used, various salts of titanium can form with materials inherent to the reaction vessel, especially if the vessel is comprised of stainless steel—these salts render the material black with time. Nevertheless, a consequence of adding these reactant materials is that in order to render the material clean and highly transparent, these excess materials and their byproducts must be removed from the polymer upon completion of the reaction.

These remnant salts and other unwanted chemicals are preferably washed from the polyisobutylene-based material by washing the polymer in a separatory funnel with salt water, with pure water and with repeated precipitations in excess polar solvent (such as isopropanol, acetone, methanol, ethanol and the like). Other well-known washing procedures can also be used. Note that if the material is not washed of salts, these hygroscopic salts begin to draw in water when the material is equilibrated in water. Voids where the salts have been trapped are readily viewed under scanning electron microscopy and these voids become filled with water as the salt is dissolved out. As water has a refractive index of approximately 1.33 and material has a refractive index of 1.53, the difference in refractive index is sufficient to render the polymer cloudy and at times totally opaque. If the material is washed appropriately, these salts are removed and voids no longer exist.

In one methodology, the polyisobutylene-based material of the optic (and possibly other parts of the ocular device described herein) is formed and molded at temperatures that are significantly less the melting point of the material by casting the material from a solution. This is accomplished by dissolving the polyisobutylene-based material in a solvent (such as hexanes, toluene, methylcyclohexane, cyclopentane, and the like) and casting the resulting solution. Because casting from solution affords control over only one side of the lens, it is difficult to accurately form a lens with opposing optical surfaces utilizing casting from solution alone. In these applications, casting from solution is preferably used to form a lens preform that is finished by compression molding.

More particularly, the solution comprising the dissolved polyisobutylene-based material is cast into a preform mold thereby forming one or more lens preforms. The shape and dimensions of the preform mold approach the geometry of the desired end product lens. The lens preform(s) is (are) removed from preform mold and placed into a compression mold. The compression mold is pressed closed and heated for a predetermined duration at temperatures that are significantly less than the melting point of the material. The heating temperature and duration are selected such that the lens preform flows to its desired final shape (with optically finished surfaces and the desired curvature) while the material maintains it's casting morphology. The end product lens is then removed from the compression mold. Once cooled, it has been found that the end product lens will maintain high transparency in the ocular environment.

The SIBS material has a melting point between 200° C. and 250° C. In this case, the heating temperature utilized during the compression molding operations is preferably in the range between 100° C. and 120° C. for a duration between 10 to 90 minutes. At these parameters, the SIBS material maintains its casting morphology, that is the domain segments remain intact and simply flow to fill the mold cavity.

Figure 10:
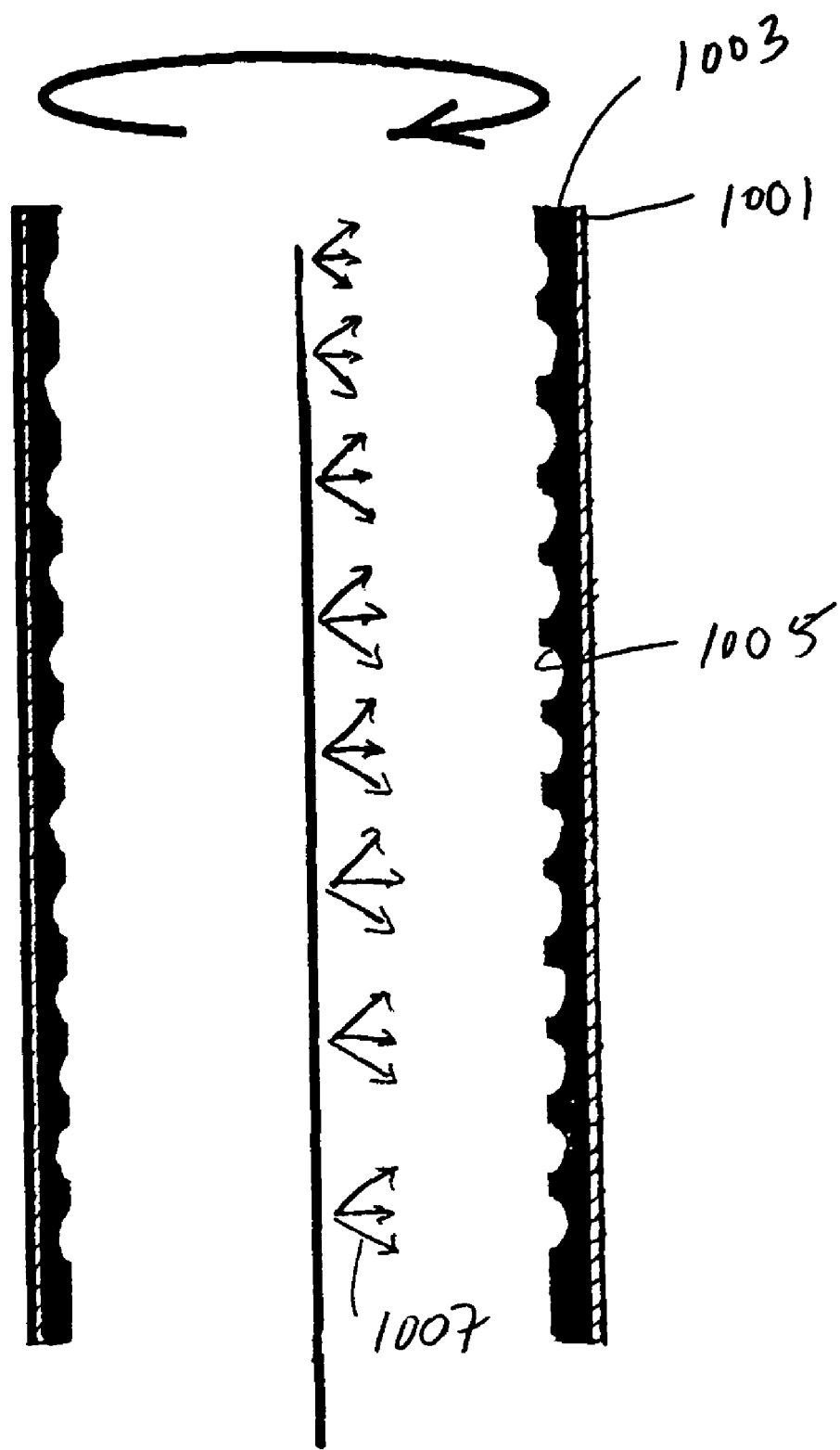
FIG. 10 is a cross-sectional schematic view of a centrifugal casting apparatus for use in fabricating an ocular lens device in accordance with the present invention.

The casting by solution operations that construct the preform preferably utilize a centrifugal casting technique wherein a sheet of the polyisobutylene-based material is cast within a rotating cylinder as shown in FIG. 10. The inside of the cylinder 1001 is lined with a Teflon® skin 1003. An array of evenly spaced indentations 1005 are milled into the inner surface of the Teflon® skin (but not through the skin) preferably using a ball mill. The rotating cylinder 1001 is supported in an oven (not shown) that is operated at a heating temperature preferably in the range between 40° C. and 60° C. The cylinder is rotated about is central axis preferably at a rotation speed of approximately 3000 RPM. As the cylinder 1001 is rotated, the polyisobutylene-based solution (for example, polyisobutylene-based material dissolved in toluene solvent at a 10% wt/wt ratio) is injected into the cylinder 1001 as pictorially represented by the arrows 1007. The rotation of the cylinder 1001 produces centrifugal forces that force the solution against the inner surface of the skin 1003 and into the indentations 1005. The process can be repeated until the desired film thickness is obtained. The film is then dried (typically requiring several hours drying time) and removed from the cylinder. The film consists of a ribbon of preform lenses (bumps) that are evenly located along the ribbon. These preform lenses approach the geometry of the desired end product lens, except that the surfaces are not optically finished nor set to the desired curvature. The lens preforms are cut out (trephined) from the ribbon and placed into a compression mold that forms the end product lens. Note that other polymeric casting techniques, such as spin casting techniques, can also be used to construct the lens preforms at low temperatures relative to the melting point of the polyisobutylene-based material.

The centrifugal casting of preform lenses together with compression molding finishing of the lenses advantageously provide a flexible, biocompatible polyisobutylene-based lens that maintains high transparency in ocular fluid over time. Such operations are also advantageous because they avoid the inefficiencies of the prior art manufacturing methods. More specifically, the use of the Teflon® skin on the inner surface of the centrifugal caster reduces the amount of cleaning that is required between mold cycles. In addition, the low temperature compression molding operations helps reduce flash formation. These features provide for improved production cost efficiencies over the prior art manufacturing methods.

In another methodology, the optic (and possibly other parts of the ocular lens device) is formed by rapidly heating the polyisobutylene-based polymer to a temperature at or near its melting point. The resultant polymer melt is added to a mold that forms the optic (and possibly other parts of the ocular lens device). The polymer and mold is quickly cooled back to room temperature for removal from the mold. The polymer may be heated in the mold, or heated outside the mold and added to the mold in its melt state. For a polymer with 10 mole percent styrene content, the heating temperature range is 150° C. to 200° C. and more preferably between 170° C. to 180° C. Preferably, the polyisobutylene-based polymer is rapidly heated in a mold to this temperature and the mold closed and pressurized to greater than 500 psi and then immediately rapidly cooled to room temperature. The rapid cooling can be accomplished by cooling coils, liquid nitrogen or the like. The entire rapid heating-cooling cycle is preferably less than three (3) minutes, and more preferably less than one (1) minute such that the optic maintains in vivo transparency.

One can speculate that forming the ocular lens by traditional thermal processing of the polyisobutylene-based material without rapid heating and cooling results in clouding in water due to the entrapment of water molecules amongst the polyisobutylene chain segments. More particularly, when such material is heated to a temperature at or near its melting temperature and then allowed to slowly cool to room temperature, the glassy segments aggregate and segregate themselves from the soft polyisobutylene segments. This phase segmentation is known to occur in these types of polymers as well as in other polymers, such as polyurethane, and the like. It is further theorized that the water molecules are trapped in the segments as when pure polyisobutylene is immersed in water it clouds, whereas polystyrene does not cloud. Further, when the polymer is heated, there is more motility or vibration in the chains, further entrapping water and hastening the clouding as well as the extent of clouding. However, the polyisobutylene-based material cast from solution seems to segregate differently and experiences minimal clouding in water.

EXAMPLE 1

An ocular lens is constructed from a polyisobutylene-based material cast from solution with a thickness of less than approximately 0.03 inches. The lens is placed in a water bath at 36° C. and maintains 95%-100% transparency in the visible spectrum over a period of two months.

EXAMPLE 2

An ocular lens is constructed from a polyisobutylene-based material cast from solution with a thickness of approximately 0.04 inches. The lens is placed in a water bath at 36° C. and a slight amount of clouding is observed by the naked eye after two days. Thereafter, lens maintains a transparency of 85%-95% in the visible spectrum over a period of two months.

EXAMPLE 3

An ocular lens is molded from polyisobutylene-based material in conjunction with rapid heating and cooling of the material with a thickness of less than approximately 0.03 inches. The lens is placed in a water bath at 36° C. and a slight amount of clouding is observed by the naked eye after two days. Thereafter, lens maintains a transparency of 85%-95% in the visible spectrum over a period of two months.

Optical clarity additives, such as mineral oil, paraffinic oil, naphthalic oil and small chains of polyisobutylene, and the like, can be added to the polyisobutylene to help fill the voids between the polyisobutylene strands that would otherwise trap water. Preferably, such additives are added to the polyisobutylene polymer at a ratio between 1% to 3% wt/wt. These optical clarity additives also help maintain the lenses highly transparent in both air and water; however, these additives are generally not desirable for implantation applications as they may leach from the polyisobutylene polymer into the ocular environment and provoke an undesirable response.

As noted above, the polyisobutylene-based material used in connection with the present invention is endowed with good biocompatibility. The biocompatibility of a polystyrene-polyisobutylene-polystyrene SIBS copolymer for the illustrative intraocular lens described herein is demonstrated below in connection with the following non-limiting example.

EXAMPLE 4

Materials and Methods: SIBS material having a triblock polymer backbone comprising polystyrene-polyisobutylene-polystyrene of mole percent styrene content 9.8%, 21.5% and 23.4%, respectively, were synthesized by living end carbocationic polymerization techniques. Also synthesized was a control material made from medical grade polydimethylsiloxane (PDMS, RI=1.41). Both the SIBS material and the PDMS material were compression molded at 160° C. into flat disks, 3 mm and 6 mm diameter, all being 300 μm thick. The disks were implanted in four groups of two New Zealand White rabbits using conventional surgical techniques. Maxitrol topical ointment was given for three days. No medications were given thereafter. Full ophthalmic examinations were performed weekly using a slit-lamp biomicroscope. Two animals with an endocapsular implant (intraocular lens) were followed until the eighth week and six animals with intracorneal and subtenon implants were followed until the twelfth week before euthanasia for histology.

Results: No inflammation, infection, toxic reaction and implant migration were observed. The cornea, sclera, iris, ciliary body, choroids, vitreous and retina remained normal in all animals. No neovascularization or fibrosis could be detected around any SIBS disks implanted intracorneally. Subtenon PDMS control implants elicited a moderate neovascularization reaction whereas the SIBS samples did not. Encapsulation was approximately 200 μm for PDMS and was well organized and consistent around the sample. In addition, gross histology showed neovascularization (an ingrowth of capillaries) radiating from the sample. The histology for the SIBS samples routinely demonstrated a loose unorganized fibrous network with variable thickness ranging from 0 to 100 μm around the sample with no signs of neovascularization. Scanning Electron Microscopy of the explanted SIBS discs showed no signs of biodegradation.

Conclusion: SIBS material is intraorbitally and intraocularly biocompatible and does not encapsulate in the eye, and thus is suitable for use in intraocular implant devices.

There have been described and illustrated herein several embodiments of intraocular lens and surgical methods associated therewith. While particular embodiments of the invention have been described, it is not intended that the invention be limited thereto, as it is intended that the invention be as broad in scope as the art will allow and that the specification be read likewise. For example, it will be recognized that adaptations may be made of the lens structures described herein. More particularly, in the event that optic portion of the lens employs one or more square edges, such edges introduce facets that can cause glare from peripheral light sources. Such glare can be eliminated by frosting the edge of the optic. Alternatively, the shape and configuration of the optic of the lens may be varied. For example, the optic may be realized by first and second lens elements that are designed to be held in place along the optical axis of the eye. The first lens element, which is located posteriorly relative to the second lens, preferably has a negative power while the second lens element has a positive power. A polymeric gel (for example, one formed of the in vivo SIBS material described herein) may be disposed between the two lens elements. One or more of the therapeutic drug agents described herein (e.g., an antiproliferative agent derived from paclitaxyl) may be added to the polymeric gel to inhibit PCO. In yet other embodiments, one or more of the therapeutic drug agents described herein (e.g., an antiproliferative agent derived from paclitaxyl) may be associated with an ancillary device implanted in vivo in the eye, such as a lens tensioning device, a small patch reservoir, or as a microcapsule. In another example, the lens devices described herein can be placed in the anterior chamber, in the posterior chamber, or in the vitreous chamber. In yet another example, the lens described herein can be used in conjunction with the natural crystalline lens (e.g., the natural crystalline lens is not removed) for eyes that suffer from severe refractive errors, or can also be used as a lens for corneal replacement, or for contact lens devices.

Moreover, while particular methods of manufacture have been disclosed, it will be understood that other manufacturing methods can be used. For example, because the copolymer materials described herein have a thermoplastic character, a variety of standard thermoplastic processing techniques can be used to for the devices described herein. Such techniques include compression molding, injection molding, blow molding, spinning, vacuum forming and calendaring, and extrusion into tubes and the like. Such devices can also be made using solvent-based techniques involving solvent casting, spin coating, solvent spraying, dipping, fiber forming, ink jet techniques and the like.

It is also contemplated that the optically transparent polyisobutylene-based material described herein (and methods of fabricating such material) can be utilized into other medical implant applications.

It will therefore be appreciated by those skilled in the art that yet other modifications could be made to the provided invention without deviating from its spirit and scope as claimed.

What is claimed is:

1. An ocular lens device comprising:
   a refractive optics structure formed from a polyisobutylene-based polymer having a triblock backbone comprising polystyrene-polyisobutylene-polystyrene, the polyisobutylene-based polymer processed to remove hygroscopic salts therefrom, wherein said refractive optics structure maintains in vivo transparency in an aqueous ocular environment for at least two months, whereby in vivo transparency means that said refractive optics structure transmits at least 80% of visible light incident thereon.

2. An ocular lens device according to claim 1, wherein:
   said refractive optics structure can be folded or rolled upon itself.

3. An ocular lens device according to claim 2, wherein:
   said refractive optics structure can be folded or rolled upon itself for introduction through a small scleral incision.

4. An ocular lens device according to claim 3, wherein:
   said small sclera incision comprises a slit having a length of 2 mm or less.

5. An ocular lens device according to claim 1, wherein:
   said polyisobutylene-based polymer further comprises a copolymer selected from the group consisting of a star-shaped block copolymer and multi-dendrite-shaped block copolymer.

6. An ocular lens device according to claim 1, further comprising:
   an optic portion and at least one haptic element that are adapted to rest within a capsular bag formed by a surgical procedure that removes the natural crystalline lens supported therein, wherein said at least one haptic element supports said optic portion.

7. An ocular lens device according to claim 6, wherein:
   said at least one haptic element comprises a plurality of haptic elements that extend from said optic portion.

8. An ocular lens device according to claim 6, wherein:
   said at least one haptic element comprises an annular surface that surrounds and extends radially outward from said optic portion.

9. An ocular lens device according to claim 8, wherein:
   said optic region is configured to be substantially disposed along a plane that is perpendicular to an optical axis of an eye, and said annular surface projects radially outward from said optic portion at an angle relative to said plane, said angle between 0 and 45 degrees.

10. An ocular lens device according to claim 9, wherein:
    said angle is between 10 and 20 degrees.

11. An ocular lens device according to claim 10, wherein:
    said angle is 15 degrees.

12. An ocular lens device according to claim 6, wherein:
    said optic portion has a convex surface and a flat surface.

13. An ocular lens device according to claim 6, wherein:
    said optic portion has a stepped wall structure at its periphery.

14. An ocular lens device according to claim 6, wherein:
    said optic portion and said at least one haptic element are formed from said material.

15. An ocular lens device according to claim 6, wherein:
    said optic portion is formed from said material, and said at least one haptic element is formed from a different material.

16. An ocular lens device according to claim 1, wherein:
    said polyisobutylene-based polymer blocks ultra-violet light.

17. An ocular lens device according to claim 1, wherein:
    said refractive optics structure is adapted for intraocular disposition in a portion of the eye, the portion of the eye selected from the group consisting of the anterior chamber of the eye, the posterior chamber of the eye, and the vitreous chamber of the eye.

18. An ocular lens device according to claim 1, wherein:
    the refractive optics structure is formed and molded at temperatures that are significantly less than the melting point of the polyisobutylene-based polymer.

19. An ocular lens device according to claim 1, wherein:
    the refractive optics structure is formed by compression molding in conjunction with rapid heating to a temperature at or near the melting point of the polyisobutylene-based polymer and rapid cooling.

20. An ocular lens device according to claim 19, wherein:
    time duration encompassing the rapid heating and the rapid cooling defines a heating-cooling cycle that is less than three minutes.

21. An ocular lens device according to claim 20, wherein:
    said heat-cooling cycle is less than one minute.

22. An ocular lens device according to claim 1, wherein:
    said refractive optics structure is formed by dissolving said polyisobutylene-based polymer in a solvent to form a solution and casting the solution.

23. An ocular lens device according to claim 22, wherein:
    the casting of the solution forms at least one lens perform that is compression molded to form said refractive optics structure.

24. An ocular lens device according to claim 1, wherein:
    said refractive optics structure is formed by compression molding at a temperature between 100° C. and 120° C.

25. An ocular lens device according to claim 1, wherein:
    said refractive optics structure is formed by casting a solution of the polyisobutylene-based polymer into a preform and compression molding of the preform.

26. An ocular lens device according to claim 25, wherein:
    the compression molding is carried out at a temperature between 100° C. and 120° C.

27. An ocular lens device according to claim 1, wherein:
    said refractive optics structure can be folded or rolled upon itself for placement into the eye.

* * * * *